United States Patent
Mahieu et al.

(10) Patent No.: US 7,328,788 B2
(45) Date of Patent: Feb. 12, 2008

(54) CONTACT LENS CARE SYSTEM

(75) Inventors: Frans Mahieu, Alpharetta, GA (US);
Lynn Goldblatt, Atlanta, GA (US);
Kim Muenzer, La Canada, CA (US);
Spencer MacKay, Agoura Hills, CA (US)

(73) Assignee: Novartis AG, Basel (CH)

( * ) Notice: Subject to any disclaimer, the term of this patent is extended or adjusted under 35 U.S.C. 154(b) by 419 days.

(21) Appl. No.: 10/969,281

(22) Filed: Oct. 20, 2004

(65) Prior Publication Data

US 2005/0087455 A1 Apr. 28, 2005

Related U.S. Application Data

(60) Provisional application No. 60/584,030, filed on Jun. 30, 2004, provisional application No. 60/558,523, filed on Apr. 1, 2004, provisional application No. 60/513,289, filed on Oct. 22, 2003.

(51) Int. Cl.
*A45C 11/04* (2006.01)
(52) U.S. Cl. .................. 206/5.1; 206/223; 220/23.83; 220/729
(58) Field of Classification Search ............. 206/5.1, 206/217, 223, 501, 486, 487, 577, 581, 514; 215/6, 10, 228; 220/4.28, 23.83, 23.86, 23.87, 220/23.89, 729
See application file for complete search history.

(56) References Cited

U.S. PATENT DOCUMENTS

| | | | | |
|---|---|---|---|---|
| 2,274,973 A | 3/1942 | Bryant | ........................ | 215/13 |
| 2,374,092 A * | 4/1945 | Glaser | ........................ | 215/6 |
| 2,690,861 A | 10/1954 | Tupper | ........................ | 222/498 |
| 2,744,649 A | 5/1956 | Smith | ........................ | 215/100 |
| 2,940,589 A | 6/1960 | Silverman | ........................ | 206/5 |
| 2,949,203 A | 8/1960 | Berg | ........................ | 215/6 |
| 3,089,500 A | 5/1963 | Stalcup | ........................ | 134/156 |
| 3,124,240 A | 3/1964 | Croan | ........................ | 206/5 |
| 3,252,492 A | 5/1966 | Marchant | ........................ | 150/5 |

(Continued)

FOREIGN PATENT DOCUMENTS

DE 198 09 757 1/1998

(Continued)

OTHER PUBLICATIONS

European Standard Search Report.

(Continued)

*Primary Examiner*—Luan K Bui
(74) *Attorney, Agent, or Firm*—Robert Ambrose; Jian Zhou

(57) ABSTRACT

An integrated lens care system including a lens case for contact lenses and a container for dispensing a lens care solution. The container includes a docking site where the lens case can be stored and then removed for use, and a retainer mechanism for releasably securing the lens case in the docked position. In example embodiments, the docking site is a chamber into which the lens case is inserted, and the retainer mechanism includes at least one protrusion that extends into the docking chamber and releasably couples to at least one recess in the lens case. In another example embodiment, the docking site is a peripheral edge of the container body where a combination lens case/closure cap mounts, and the retainer mechanism includes a snap-fit coupling at the peripheral edge.

50 Claims, 13 Drawing Sheets

U.S. PATENT DOCUMENTS

| | | | |
|---|---|---|---|
| 3,326,358 A | 6/1967 | Singleton | 206/5 |
| D208,166 S | 7/1967 | Hueber et al. | D57/1 |
| 3,339,047 A | 8/1967 | Rys et al. | 200/153 |
| 3,804,233 A | 4/1974 | Gregg, Jr. | 206/19.5 R |
| 3,877,598 A | 4/1975 | Hazard | 215/224 |
| 3,927,782 A | 12/1975 | Edwards | 215/100 |
| 3,966,076 A | 6/1976 | Kroger et al. | 220/20 |
| 4,002,275 A | 1/1977 | Crowle et al. | 222/543 |
| 4,036,357 A | 7/1977 | Czelen | 206/5.1 |
| D246,896 S | 1/1978 | Plummer | D9/100 |
| 4,195,728 A | 4/1980 | Cardamone | 206/45.33 |
| 4,235,343 A | 11/1980 | Thompson | 215/6 |
| 4,429,786 A | 2/1984 | Hucal | 206/5.1 |
| 4,563,186 A | 1/1986 | Flynn et al. | 8/137 |
| 4,640,423 A | 2/1987 | Mednis | 215/10 |
| D289,923 S | 5/1987 | Hoogesteger | D24/9 |
| 4,700,729 A | 10/1987 | Thaler | 134/139 |
| 4,721,124 A | 1/1988 | Tuerkheimer et al. | 134/138 |
| 4,776,972 A | 10/1988 | Barrett | 252/90 |
| 4,795,028 A * | 1/1989 | Wittig et al. | 206/5.1 |
| 4,856,647 A | 8/1989 | Dahne | 206/5.1 |
| 4,905,819 A | 3/1990 | Clements et al. | 206/5.1 |
| 4,909,382 A | 3/1990 | Cuppari | 206/5.1 |
| 4,925,017 A | 5/1990 | Jessen | 206/5.1 |
| 4,951,811 A | 8/1990 | Lines | 206/5 |
| 4,966,296 A | 10/1990 | Farrell | 220/23.4 |
| 5,002,179 A | 3/1991 | Dhala | 206/5.1 |
| 5,050,757 A | 9/1991 | Hidding et al. | 220/23.83 |
| 5,065,875 A | 11/1991 | Balavich | 215/10 |
| 5,085,330 A | 2/1992 | Paulin | 215/6 |
| D328,246 S | 7/1992 | Nottingham et al. | D9/520 |
| 5,127,517 A | 7/1992 | Clements et al. | |
| 5,129,520 A | 7/1992 | Gaspar | 206/534 |
| 5,143,234 A | 9/1992 | Lohrman et al. | 215/235 |
| 5,174,534 A | 12/1992 | Mitchell | 248/311.2 |
| 5,186,317 A | 2/1993 | Ryder et al. | 206/5.1 |
| 5,211,299 A | 5/1993 | Manfredonia | 215/11.1 |
| 5,312,014 A | 5/1994 | Hamlin | 220/703 |
| 5,415,275 A | 5/1995 | Girimont | 206/5.1 |
| D362,390 S | 9/1995 | Weiler | D9/520 |
| D379,714 S | 6/1997 | Cerny et al. | D3/264 |
| 5,647,481 A | 7/1997 | Hundertmark et al. | 206/219 |
| D404,915 S | 2/1999 | Kornick et al. | D3/264 |
| D405,260 S | 2/1999 | Kornick et al. | D3/264 |
| 6,073,757 A | 6/2000 | Kornick et al. | 206/5.1 |
| 6,289,906 B1 | 9/2001 | Vanden Dries et al. | 134/117 |
| 6,536,453 B2 | 3/2003 | Vanden Dries et al. | 134/117 |
| 2002/0020437 A1 | 2/2002 | Vanden Dries et al. | 134/117 |

FOREIGN PATENT DOCUMENTS

| | | |
|---|---|---|
| EP | 0 544 381 | 6/1993 |
| FR | 2 633 907 | 1/1990 |
| FR | 88609 | 10/1995 |
| WO | WO 93/20730 | 10/1993 |
| WO | WO 93/25453 | 12/1993 |
| WO | WO 95/34231 | 12/1995 |

OTHER PUBLICATIONS

International Search Report.

Endolthelial Cell Transplantation and Growth Behavior of the Human Corneal Endothelium, Katrin Engelman, et al., vol. 96, No. 9, Sep. 9, 1999, pp. 555-562.

Effect of Donor Age on Morphologic Variation of Cultured Human Corneal Endothelial Cells, K. Miyata, et al, vol. 20, No. 1, Jan. 2001, pp. 59-63.

Transplantation of Corneal Endothelial Cells, (abstract) Nippon Ganka Gakkai Zasshi, vol. 106, No. 12, Dec. 2002, pp. 805-836.

PCT Search Report.

* cited by examiner

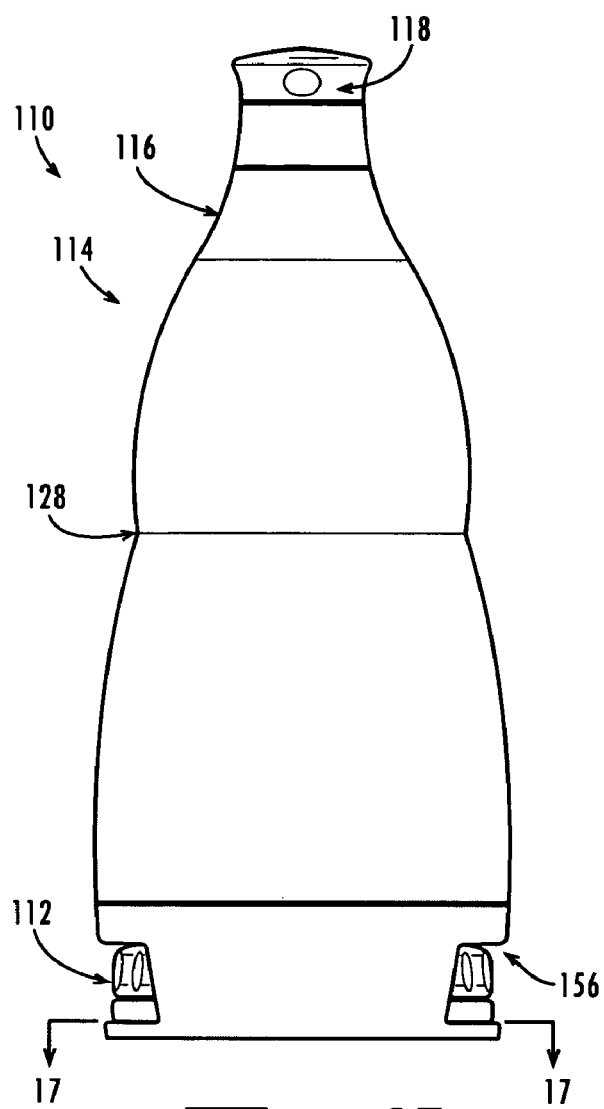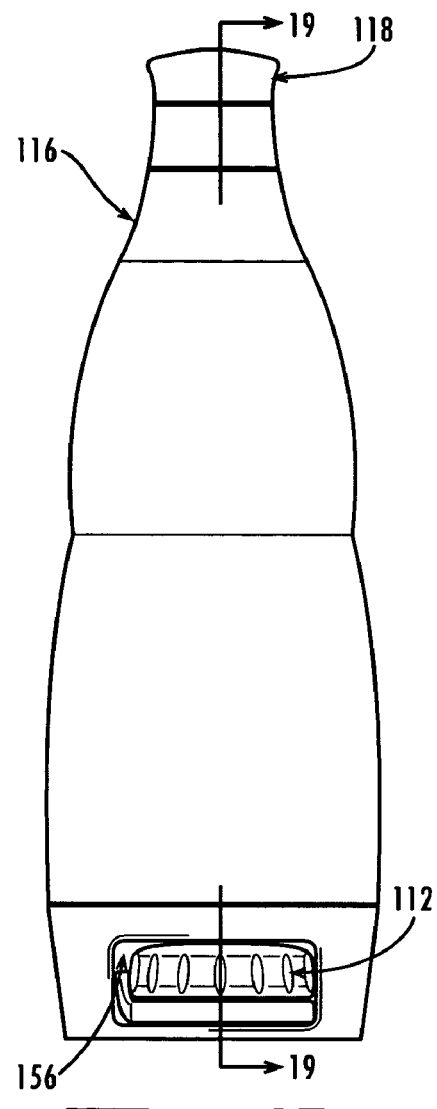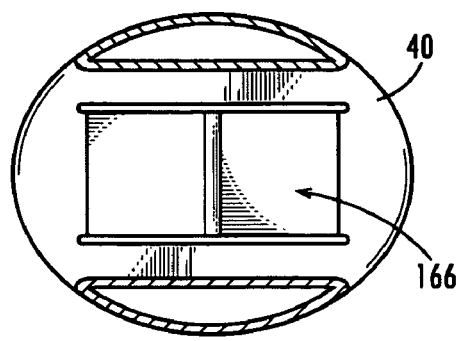

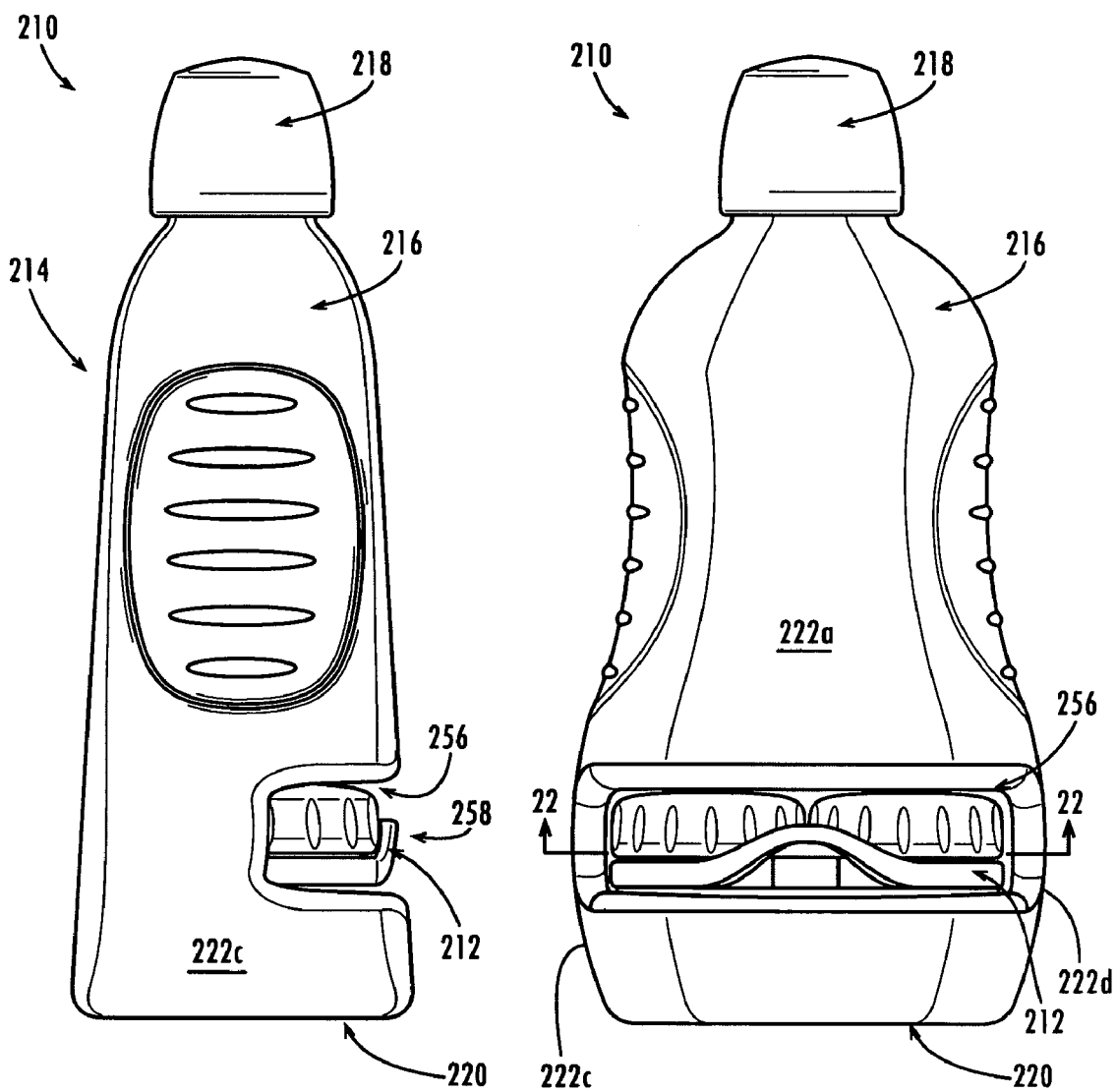
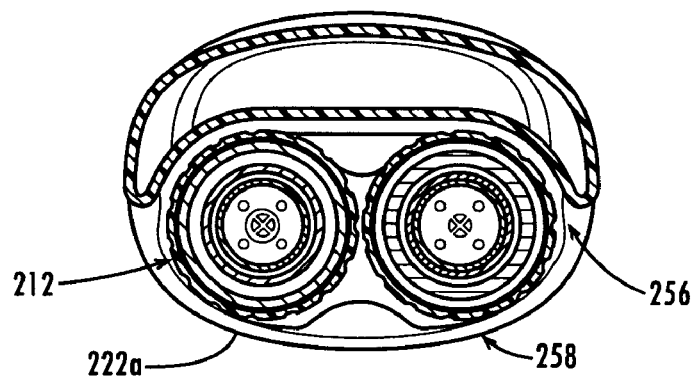

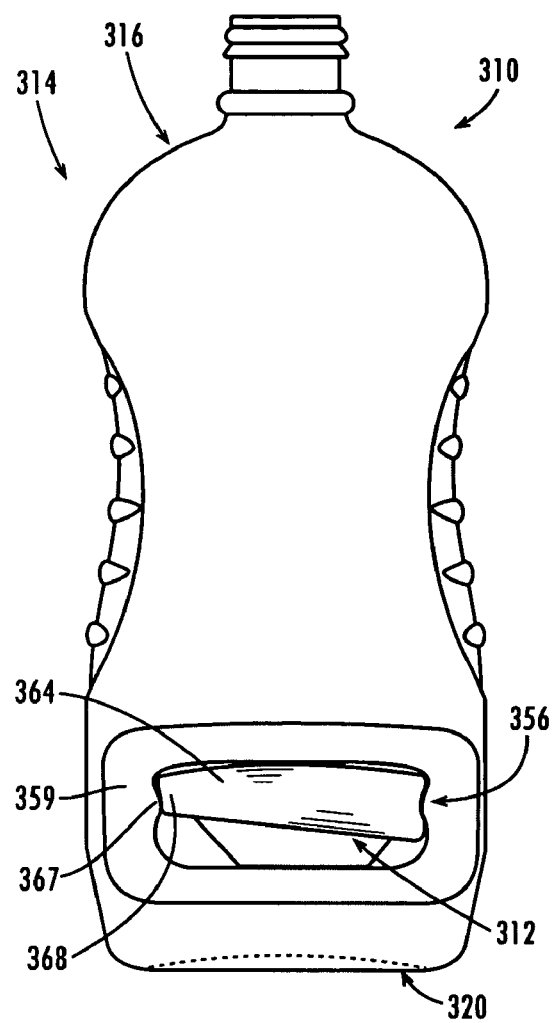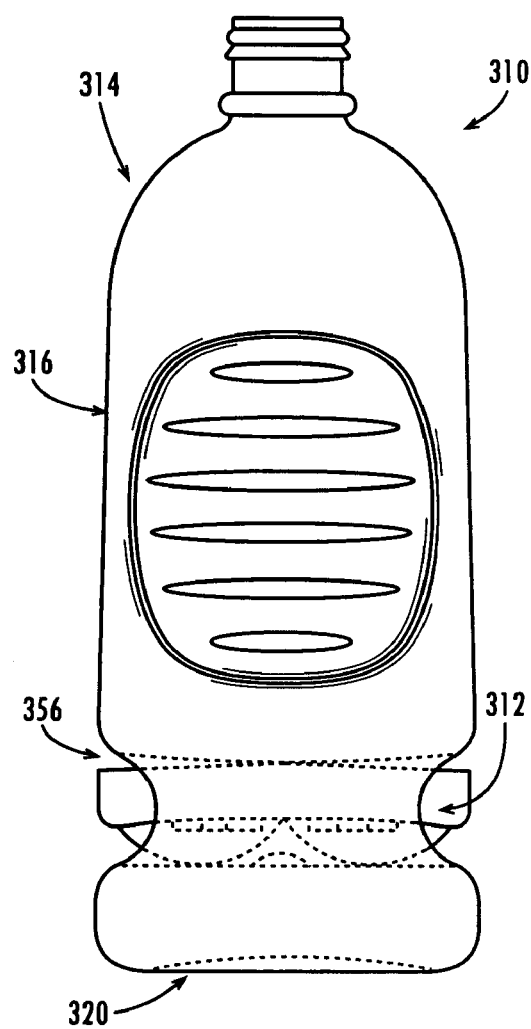
Fig. 27
Fig. 28

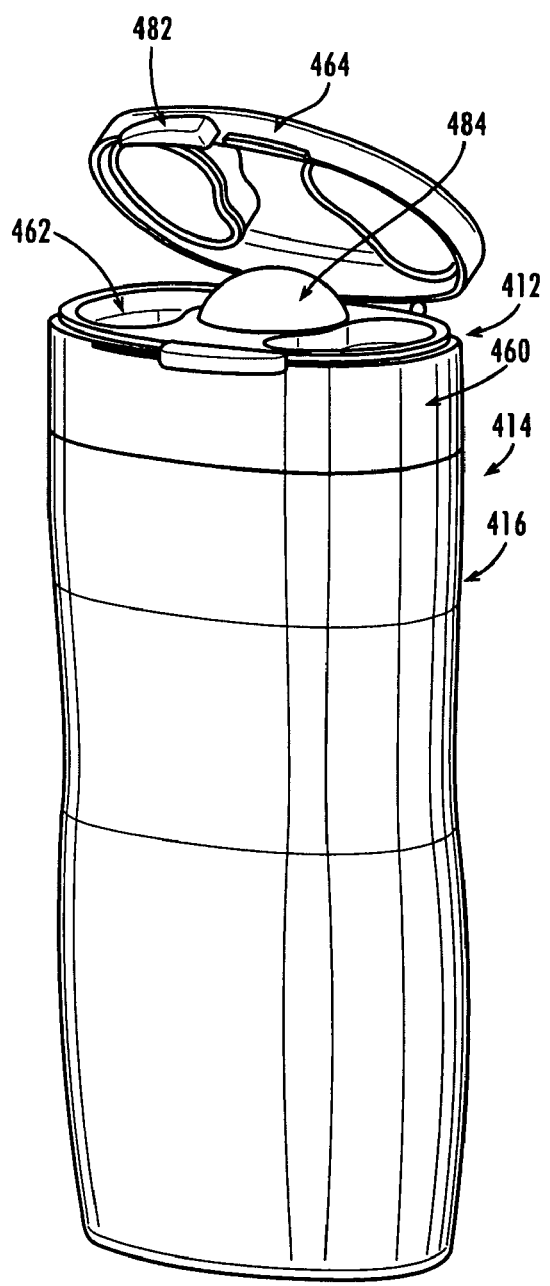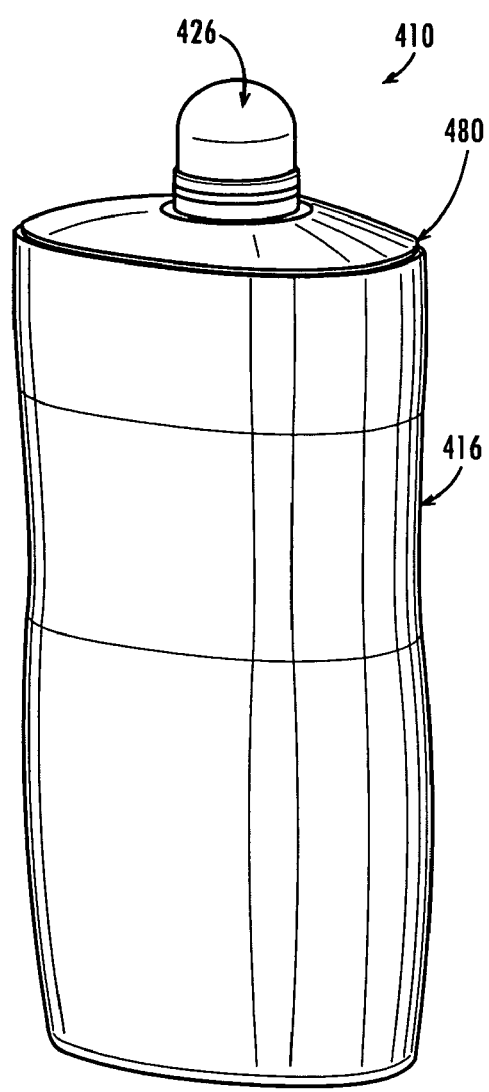
Fig. 29
Fig. 30

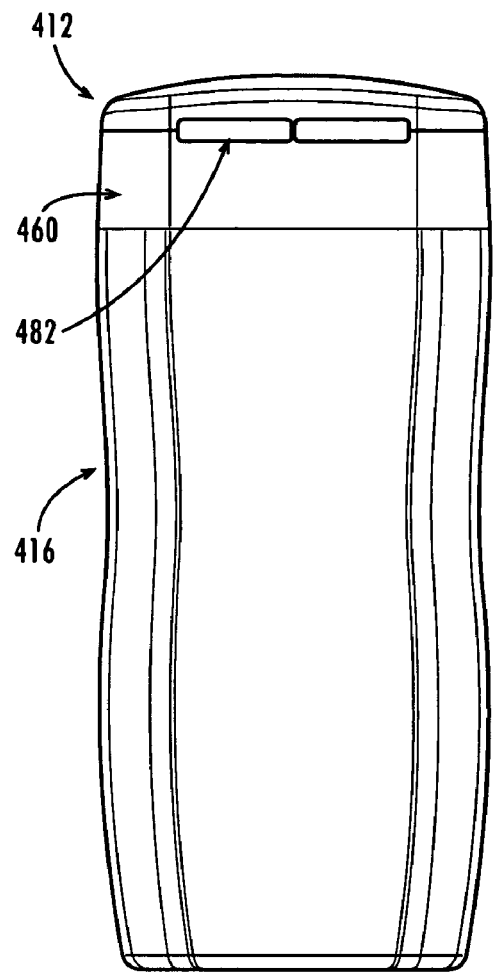
Fig. 31
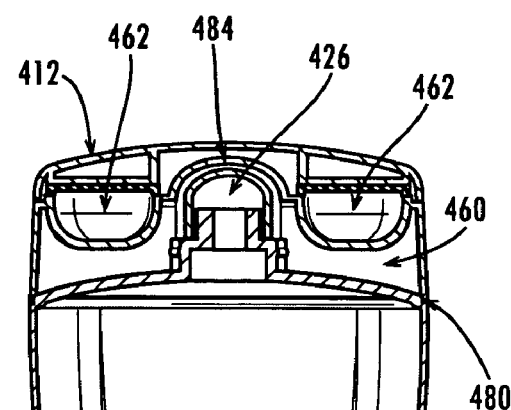
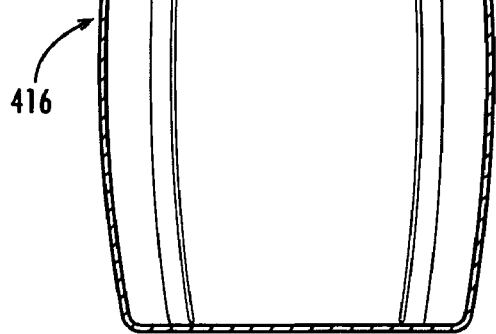
Fig. 33
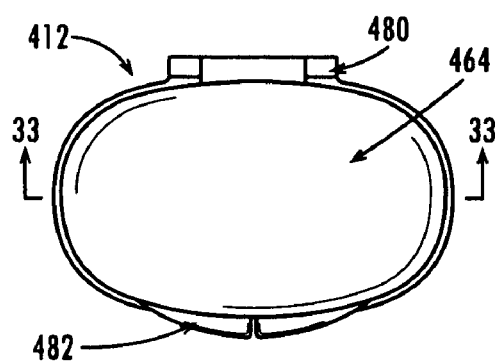
Fig. 32

CONTACT LENS CARE SYSTEM

CROSS-REFERENCE TO RELATED APPLICATIONS

This application claims priority to U.S. Provisional Patent Application Ser. No. 60/513,289 filed Oct. 22, 2003, to U.S. Provisional Patent Application Ser. No. 60/558,523 filed Apr. 1, 2004, and to U.S. Provisional Patent Application Ser. No. 60/584,030 filed Jun. 30, 2004; which applications are hereby incorporated herein by reference in their entireties. Concurrently filed U.S. patent application Ser. No. 10/969,255 filed Oct. 20, 2004 is also incorporated herein by reference in its entirety.

TECHNICAL FIELD

This invention relates to systems for care of ophthalmic lenses and, in particular, to containers for the lenses and for lens care solutions.

BACKGROUND OF THE INVENTION

Contact lenses provide a means for vision correction for a wide range of consumers. The advantages of contact lens wear are numerous. Improved convenience and improved appearance in comparison to spectacle glasses are probably the two most important advantages to most consumers. However, contact lenses require stringent care regimes in order to ensure comfort and avoid ocular infections. Proper care of contact lenses typically requires the consumer to periodically clean, disinfect, and/or rinse the lenses. Cleaning usually refers to removal of lipids, proteins or other matter which has become affixed to a lens. Disinfecting usually refers to inactivating of harmful bacteria or fungi whenever the lenses are removed from the eye, which is usually on a daily basis. Cleaning typically occurs less frequently than disinfecting, with a weekly cleaning regime being most common. Rinsing usually refers to removing debris from the lens before placing the lens in the eye.

Disinfecting, cleaning and/or rinsing of lenses often occur by immersing a lens in an appropriate lens care solution (for example, a single- or multiple-purpose care solution) in a contact lens case. Such lens cases can be used to store contact lenses between use periods. When it is desired to treat contact lenses, the appropriate contact lens care composition is removed or dispensed from a bottle or container including the composition and passed into the contact lens case in which the contact lenses have been placed. Contact lenses are often left in the lens care solution in the lens case for an extended time, for example, overnight or at least several hours. After treatment, the contact lenses are ready for wear in the eyes of the user.

The proper care of contact lenses presents the user with a substantial inconvenience in handling and storing at least two containers—one bottle for retaining a lens care solution and one lens case for treating and storing the lenses. In particular, because the solution bottle and the lens case are separate components, their organization and portability in-home and out-of-home can be challenging. For example, in in-home situations, an appropriately sized shelf space is required for organizing and storing these multiple components. Moreover, one of the lens care components may become misplaced or otherwise unavailable. In out-of-home situations (e.g., when traveling or at work), one of the lens care components can quite easily be misplaced or not packed, in particular under the circumstance where a lens treatment requires extended time.

There have been numerous attempts at improving contact lens care systems. For example, systems have been suggested in, for example, U.S. Pat. Nos. 2,940,589; 3,326,358; 4,429,786; 5,127,517; 6,073,757; 6,536,453; Des. 405,260; and Des. 404,915; and published PCT International Patent Application No. WO 95/34231. However, there remain problems with commercially available contact lens care systems in view of storage, portability, convenience and aesthetic appeal.

Therefore, it would be beneficial to provide a system in which all of the lens care components are better organized for storage, portability, and easy access and use. It is to the provision of a system meeting these and other needs that the present invention is primarily directed.

SUMMARY OF THE INVENTION

Generally described, the present invention includes an integrated lens care system for use with contact lenses and solutions for cleaning, disinfecting, and/or rinsing the lenses. The lens care system includes a lens case and a solution dispensing container having a docking site, preferably an openly accessible docking site, for releasably securing the lens case preferably in an orientation providing upright level storage of one or more contact lenses. In this way, the lens case can be safely secured at the container docking site during travel, storage on a shelf, etc., thereby providing enhanced convenience to the user.

In several example embodiments of the invention, the docking site is provided by a chamber such as a tunnel or cave formed in the container. A retainer mechanism including an engagement member releasably secures the lens case in the docking chamber. For example, the engagement member may be provided by a protrusion between two resiliently flexible panels extending from a lower chamber surface. And the protrusion may be matingly received in a recess in the lens case to hold the case in the docking chamber. Alternative embodiments of the invention in which the retainer mechanism is positioned and/or constructed differently are included and described herein.

In another example embodiment, the lens case is removably attachable to the top of the container so that it doubles as the container cap. The docking site is defined at, and the retainer mechanism includes, an upper peripheral edge that releasably couples to the lens case body, preferably with a snap fitting and/or a twist-and-lock fitting.

In one aspect, the invention is the solution container including the hollow body for the solution, the container cap, the container base, and the docking site with features for releasably securing the lens case. In another aspect, the invention is the lens case with features for releasably securing the lens case at the docking site. And in yet another aspect, the invention is the combination of the lens case and the container, with the features just described.

The present invention provides the foregoing and other features, and the advantages of the invention will become further apparent from the following detailed description of the preferred embodiments and the accompanying drawing figures. The detailed description and drawing figures are merely illustrative of the invention and do not limit the scope of the invention, which is defined by the appended claims and equivalents thereof.

BRIEF DESCRIPTION OF THE DRAWINGS

FIG. 16 is a front elevation view of a lens care system according to a second example embodiment of the present invention, showing a lens case docked in a docking chamber of a solution dispensing container.

FIG. 17 is a cross section view of the engagement member of the lens care system taken at line 17-17 of FIG. 16.

FIG. 18 is a right elevation view of the lens care system of FIG. 16.

FIG. 20 is a right elevation view of a lens care system according to a third example embodiment of the present invention, showing a lens case docked in a docking chamber of a solution dispensing container.

FIG. 21 is a front elevation view of the lens care system of FIG. 20.

FIG. 22 is a cross section view of the lens care system taken at line 22-22 of FIG. 21.

FIG. 27 is a front elevation view of a lens care system according to a fourth example embodiment of the present invention, showing a lens case docked in a docking chamber of a solution dispensing container.

FIG. 28 is a right elevation view of the lens care system of FIG. 27.

FIG. 29 is a perspective view of a lens care system according to a fifth example embodiment of the present invention, showing a lens case docked at a docking site of a solution dispensing container.

FIG. 30 is a perspective view of the lens care system of FIG. 29, with the lens case removed.

FIG. 31 is a front elevation view of the lens care system of FIG. 29.

FIG. 32 is a plan view of the lens care system of FIG. 29.

FIG. 33 is a cross section view of the lens care system taken at line 33-33 of FIG. 32.

DESCRIPTION OF EXAMPLE EMBODIMENTS

Figure 1:
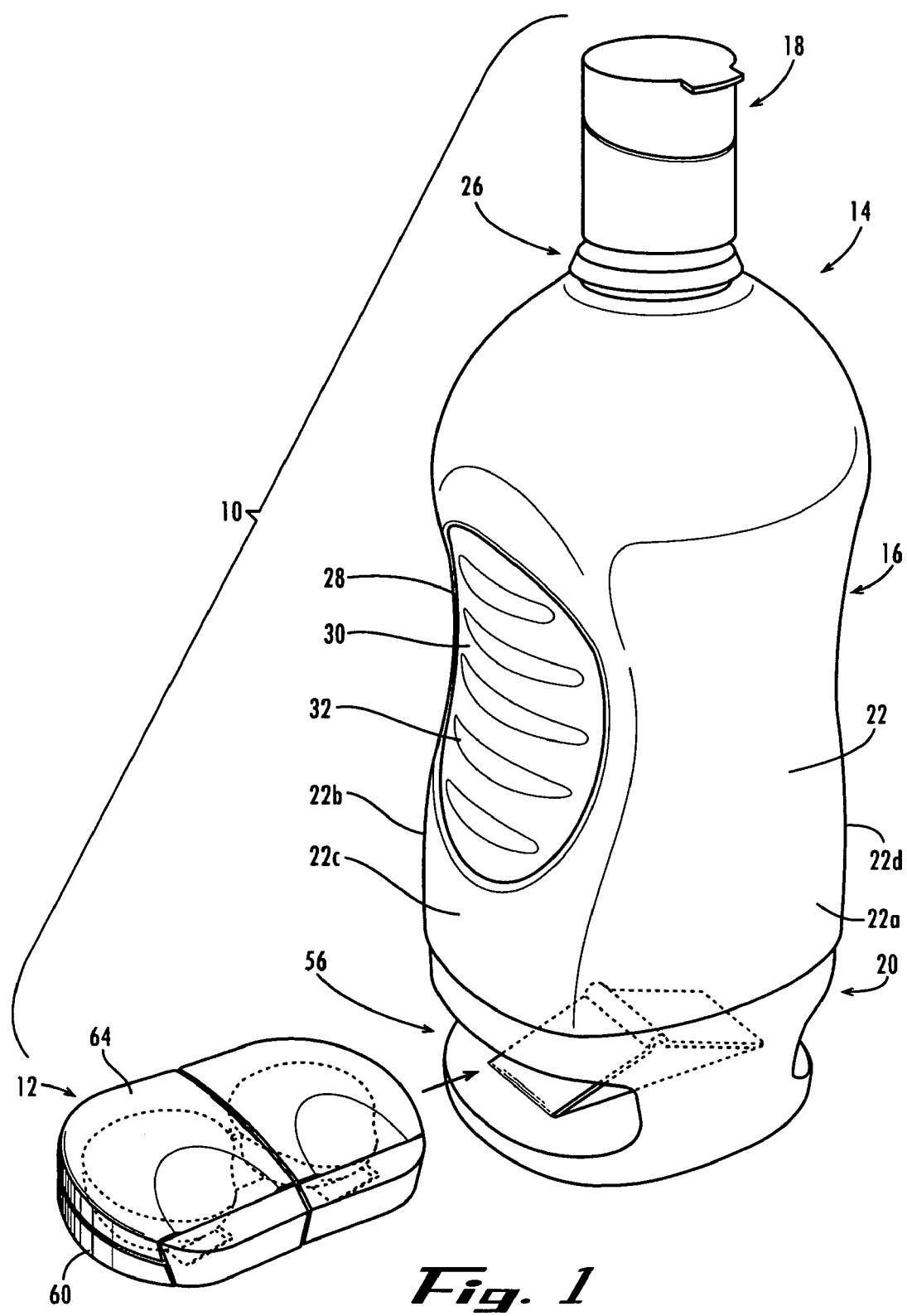
FIG. 1 is a perspective view of a lens care system according to a first example embodiment of the present invention, showing a lens case being inserted into a docking chamber in a solution dispensing container.
Figure 2:
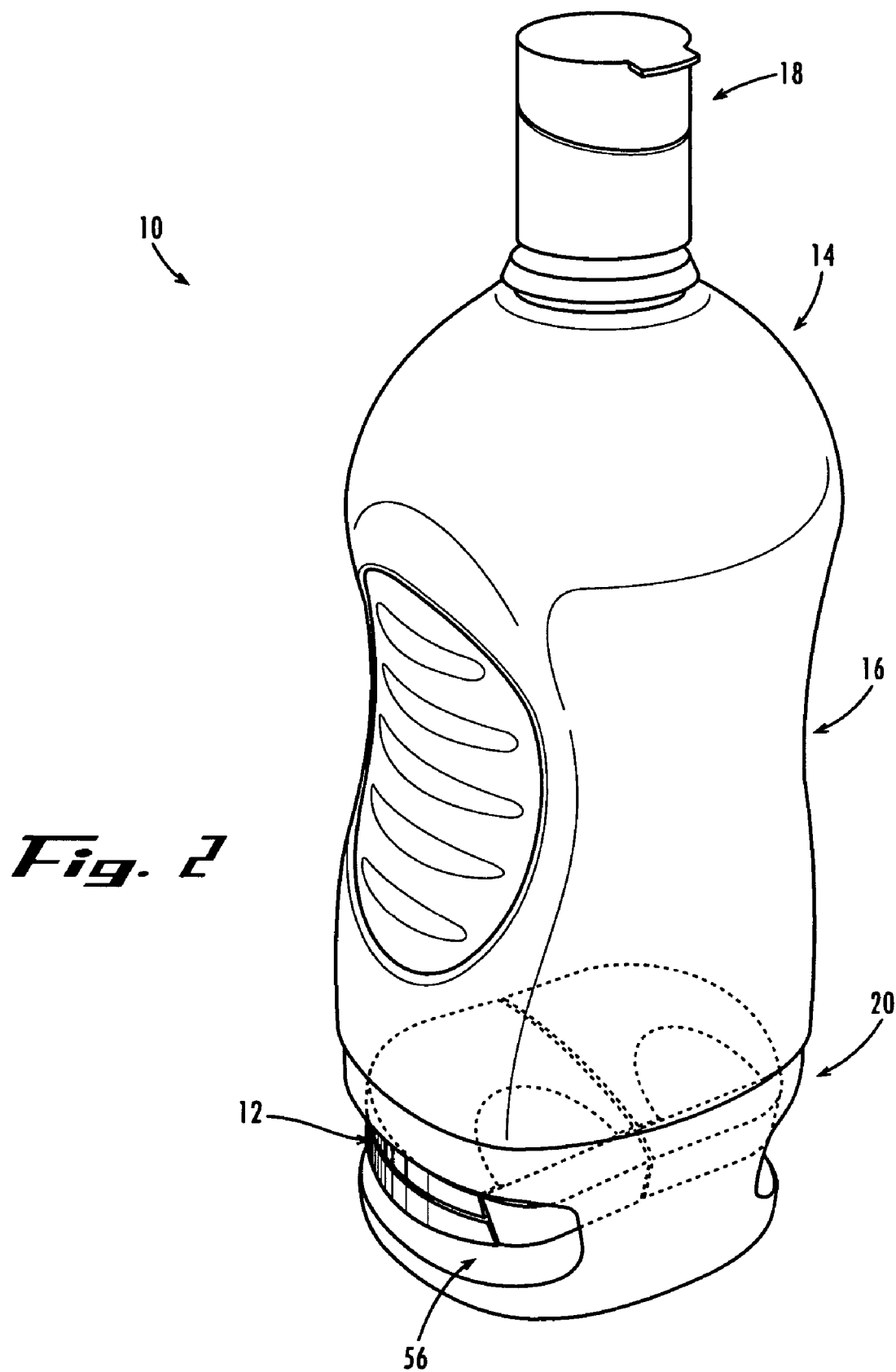
FIG. 2 is a perspective view of the lens care system of FIG. 1, showing the lens case docked in the docking chamber.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term, and reference to a particular numerical value includes at least that particular value, unless the context clearly dictates otherwise. In addition, use of the term "or" is to be construed to mean "and/or."

With reference now to the drawings, FIGS. 1-15 show an integrated lens care system 10 according to a first example embodiment of the present invention. The system 10 generally includes a lens case 12 and a solution-dispensing container 14 having a docking site for releasably securing the lens case. The lens case 12 stores conventional contact lenses and the dispensing container 14 holds a conventional lens care solution. Other components, for example, additional solution dispensers, mirrors, and lens handling devices, may also be included.

The container 14 includes a hollow body 16, a cap 18, and a base 20. The hollow body 16 is formed by a peripheral side wall 22, a bottom wall 24, and an upper neck 26 defining an open mouth for receiving and dispensing the lens care solution into and out of the hollow body. The cap 18 attaches to the neck 26 and provides a substantially liquid-impermeable seal for the mouth. The base 20 extends downwardly from the hollow body 16 adjacent the bottom wall 24. The container 14 preferably has a smoothly-contoured outer surface with no sharp corners or edges.

In a typical commercial embodiment, the hollow body 16, the cap 18, and the base 20 of the container 14 are each integrally formed as single pieces. These components of the container 14 are preferably made (e.g., molded) from a thermoplastic polymeric material, for example, high density polyethylene, low density polyethylene, polypropylene, poly(ethylene terephthalate) or the like. The material selected for the hollow body 16 preferably has sufficient flexibility and resiliency to permit the user to squeeze opposed sides of the hollow body inwardly to squirt or dispense lens care solution out of the container. While the container 14 can be provided in various sizes, its dimensions are preferably selected to permit a juvenile or adult human user to readily grasp and squeeze the container with one hand to dispense lens care solution. In an example form, the container 14 has a height of about 18 cm (from the bottom wall to the mouth), a width of about 7 cm (from one side wall to the other side wall), and a depth of about 6 cm (from the front face to the back face); and has a contained volume of about 355 ml.

The container 14 may hold any of a wide variety of lens care solutions for dispensing. For example, the container may contain disinfecting solutions such as hydrogen peroxide, cleaning solutions, artificial tear solutions, ophthalmic treatment solutions, wetting solutions, rinsing solutions, single-purpose solutions, multiple-purpose solutions, and the like. Thus, the invention is not limited by the choice of solution in the dispenser.

As shown in FIG. 1, the peripheral side wall 22 of the hollow body 16 preferably comprises a thin shell formed by a front wall 22*a*, a back wall 22*b*, and two opposing side walls 22*c* and 22*d*. The two opposing side walls 22*c* and 22*d* each have a recessed portion 28, with the opposing recessed portions cooperatively functioning as gripping areas for a user to easily grasp and handle the container.

The recessed gripping portions 28 may be inwardly curved surfaces, notches, or indentations that a narrower horizontal cross-section of the peripheral side wall 22 sufficient to enable a user to easily grasp the container. The recessed gripping portions 28 preferably have surfaces 30 with increased gripping friction provided by surface irregularities 32, for example, ribs, ridges, raised dots, raised lines, indented grooves or dots, surface textures, or combinations thereof. The gripping surfaces 30 may be integrally formed with the container 14 or applied separately as additional layers.

In the example embodiment shown, the recessed gripping surfaces 30 have surface irregularities 32 in the form of a series of outwardly raised ribs extending generally parallel to the bottom wall 24, which provides a more secure grip. The gripping surfaces 30 are preferably recessed about 5 mm, at their deepest portion from the side walls 22*c* and 22*d*, and the ribs protrude about 1-2 mm from the gripping surfaces 30. The recessed gripping surfaces 30 preferably have a generally constant radius of curvature, or a radius of curvature that progressively decreases toward the uppermost portions of the gripping surfaces, to provide the user with an outwardly and downwardly flared surface of contact, for enhanced stability and gripping contact when lifting the container and tipping it to dispense lens care solution therefrom.

The container body 16 preferably has a cylinder or cylinder-like shape. The top view and horizontal cross-sections (i.e., cross-sections parallel to the bottom of the container) of the lens care system generally can have a perimeter (periphery) of any shape, such as, for example, polygon, circle, oval, or oval-like. Oval-like, as used herein, refers to ovals, egg shapes, and the like. The horizontal-cross-sectional shape defined by the periphery of the container of the invention is preferably a continuous curve which promotes the convenience, ergonomics and aesthetic appeal of the present invention. It should be understood that horizontal cross-sections at and/or near its openly accessible docking site can be broken or partial shapes of, for example, a polygon, a circle, an oval, or an oval-like. In a preferred embodiment, the top-view and horizontal cross-sections of the container have oval-like shapes (i.e., ellipses or the likes).

Figure 3:
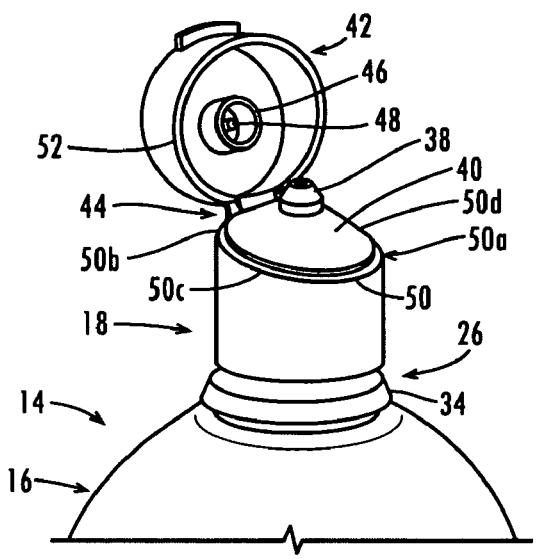
FIG. 3 is a perspective view of an upper portion of the dispensing container of FIG. 1, showing features of the cap.
Figure 4:
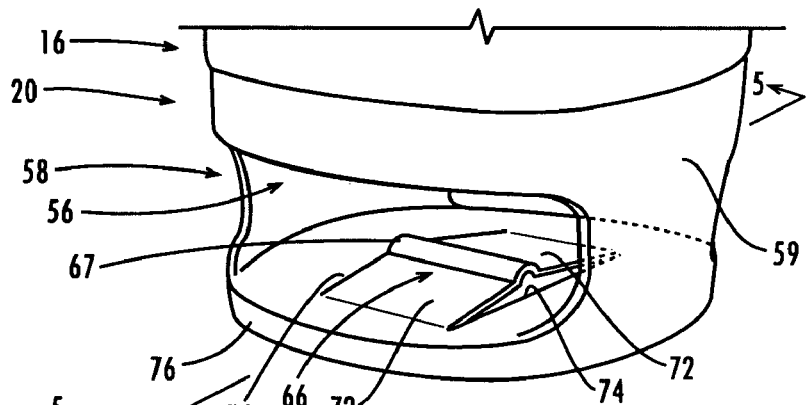
FIG. 4 is a perspective view of a lower portion of the dispensing container of FIG. 1, showing details of the engagement member and the docking chamber.
Figure 5:
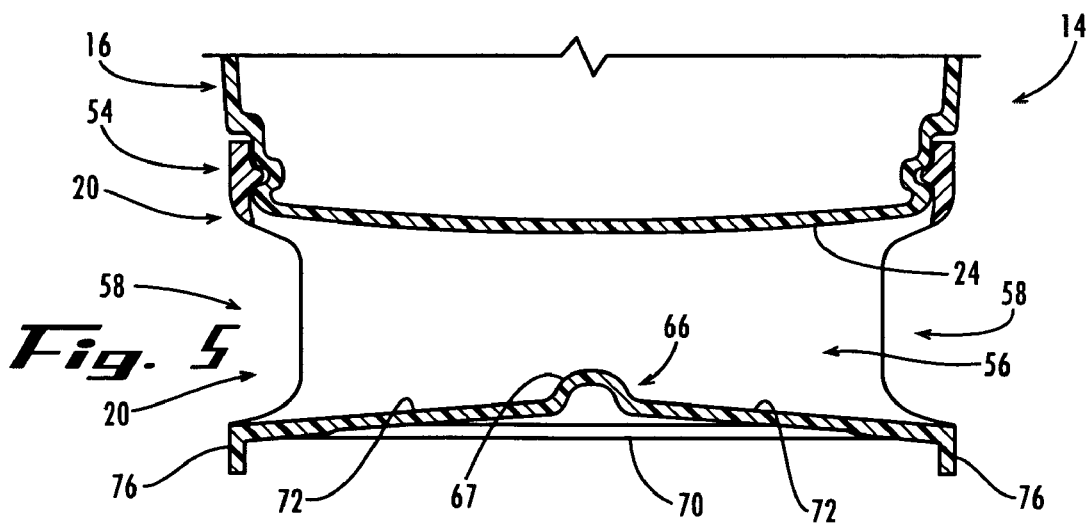
FIG. 5 is a cross section view of the dispensing container portion taken at line 5-5 of FIG. 4, showing details of the engagement member and the docking chamber.
Figure 14:
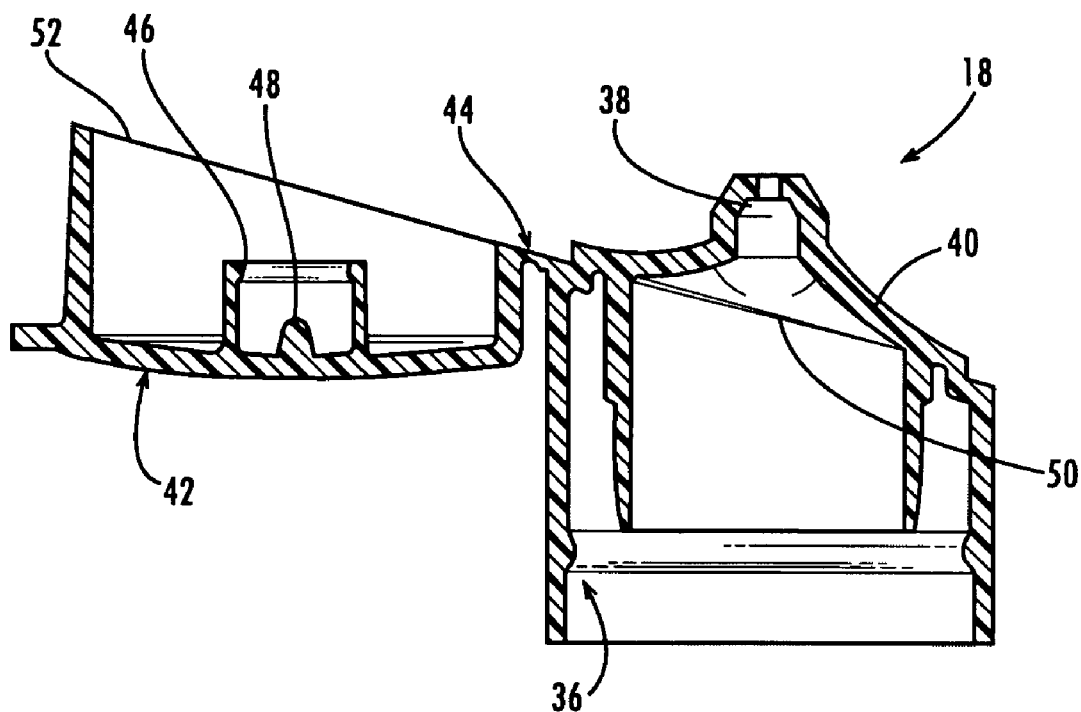
FIG. 14 is a cross section view of the cap of the container of FIG. 1.
Figure 15:
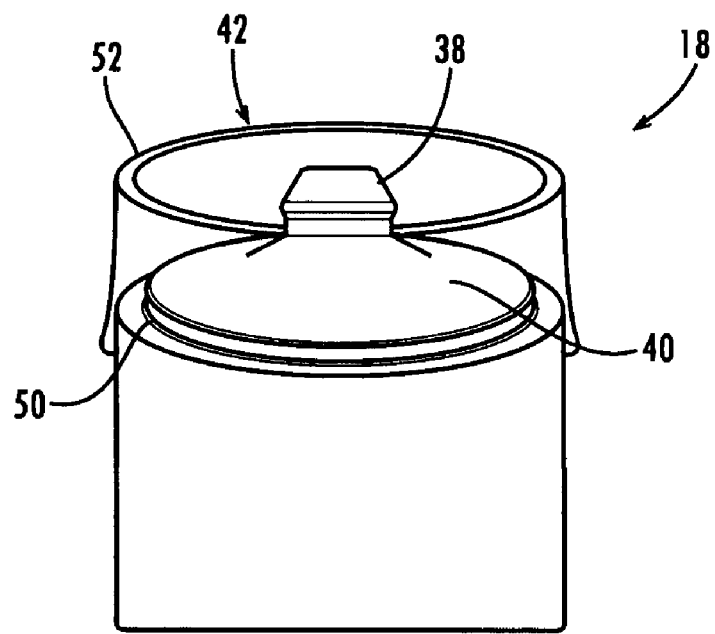
FIG. 15 is a front elevation view of the cap of FIG. 14.
Figure 19:
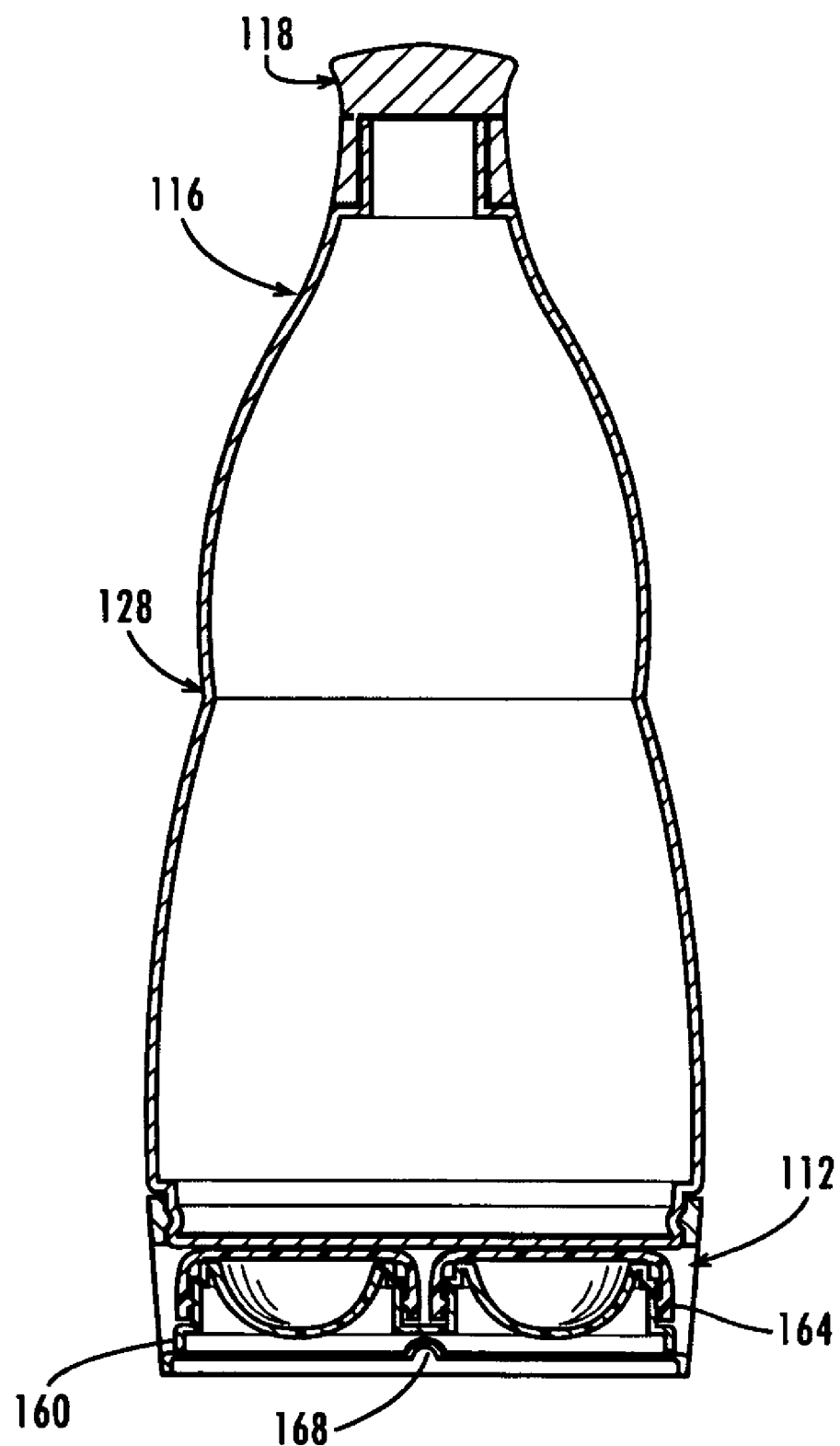
FIG. 19 is a longitudinal cross section view of the lens care system of FIG. 16.
Figure 23:
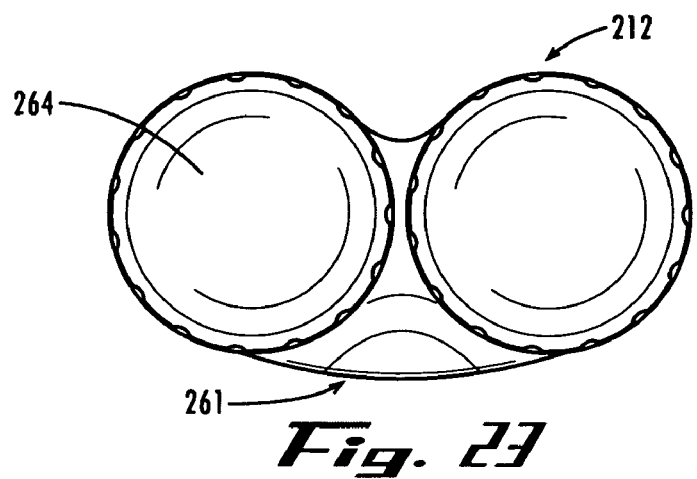
FIG. 23 is a plan view of the lens case of the lens care system of FIG. 20, showing the grasping handle.
Figures 24, 25:
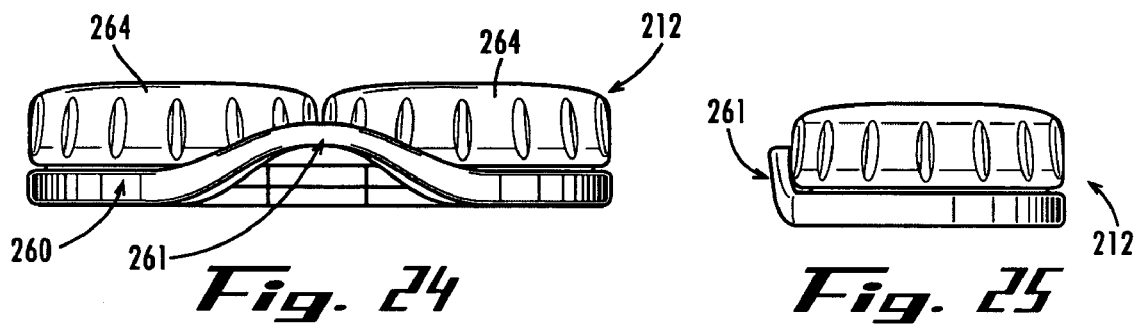
FIG. 24 is a front elevation view of the lens case of FIG. 23.
FIG. 25 is a right elevation view of the lens case of FIG. 23.
Figure 26:
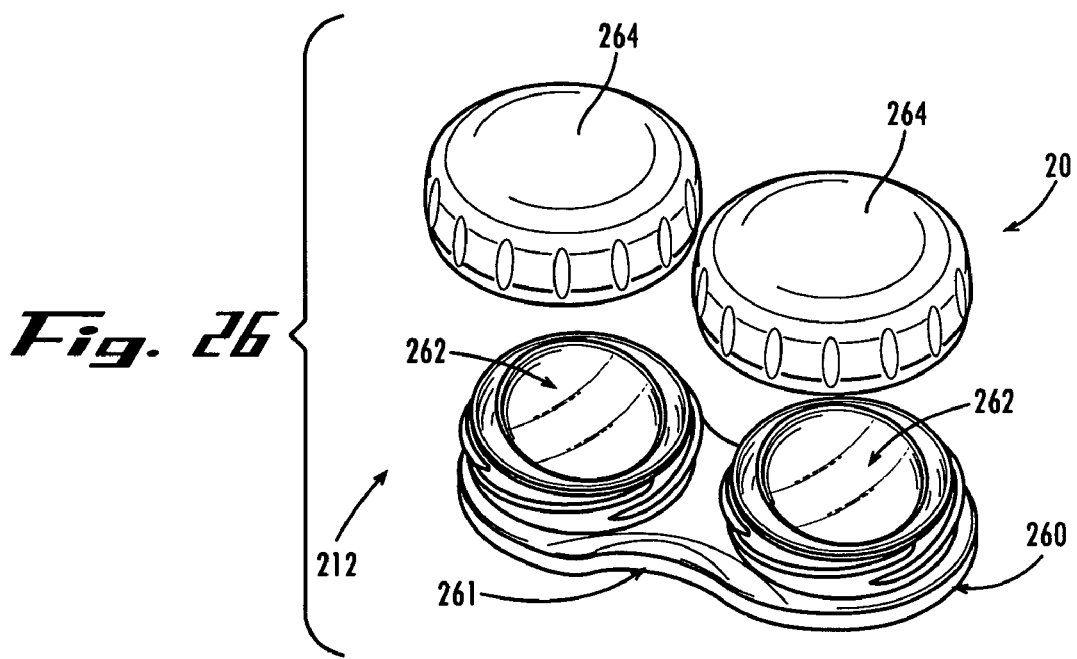
FIG. 26 is a perspective view of the lens case of FIG. 23.

FIGS. 3, 14, and 15 show details of the cap 18 of the container 14. The cap 18 is preferably secured to the neck 26 of the container 14 over its open mouth. The neck 26 of the container 14 preferably comprises a circumferential flange 34 for handling during manufacture and filling, and to resist tampering and removal of the cap 18. The cap 18 preferably comprises a snap fitting 36 for semi-permanent attachment to mating snap-fitting components on the neck 26 of the container 14, so that the cap cannot be easily removed from the container once installed (to prevent tampering with the contents and resultant loss of sterility). Preferably, the cap 18 further includes a sealing rim or surface adapted to sealingly mate with a periphery of the dispensing opening of the container. Alternatively, the cap 18 may be secured to the neck 26 by a threaded coupling, by adhesive or solvent bonding, by thermal or ultrasonic welding, by one or more connectors, or it may be integrally formed with the container.

The cap 18 preferably further comprises a dispensing nozzle or nipple 38, defining a small orifice for dispensing a narrow stream of the lens care solution therefrom. The nozzle 38 is preferably arranged generally centrally, or slightly off-center, on an upper flange 40 of the cap 18. The cap 18 preferably also comprises an openable and closable cover 42, to allow the user to selectively open and close the nozzle 38, for dispensing solution or sealing the container's contents. The cover 42 is preferably connected to the rest of the cap 18 by a living hinge 44, which preferably includes resilient biasing means to bias the cover toward its open and closed positions. The cover 42 preferably further comprises a generally cylindrical closure flange 46, which closely receives the beveled upper end of the nozzle 38 when the cover is closed, and a central stopper pin 48 positioned concentrically within the closure flange for aligning with and being received in the nozzle's dispensing orifice when the cover is closed to seal against leakage. Preferably, the closure flange 46 and the stopper pin 48 positively engage and disengage the nozzle 38 with an audible or tactile "click" or other user-recognizable indicator of engagement and disengagement.

The upper flange 40 has a peripheral edge 50 defining a plane that is angled from horizontal (when the cap 18 is on the container 14 and the container is upright and resting on a flat surface). The angle of the upper flange 40 is preferably about 10 to 20 degrees from horizontal, and more preferably about 15 degrees. The cap 18 is preferably oriented on the container 14 with the lowest portion 50*a* of the peripheral edge generally aligned with the front side wall 22*a* of the container, and configured with the hinge 44 at the highest portion 50*b* of the peripheral edge.

In this way, the intermediate portions 50*c* and 50*d* between the highest and lowest portions of the peripheral edge 50 are generally aligned with the recessed gripping portions 28 of the side walls 22*c* and 22*d*. This arrangement provides an improved ability for the user to view and direct the flow of dispensed lens care solution when grasping the recessed gripping portions 28 of the container 14.

In an alternative embodiment, the nozzle 38 is arranged off-center on the upper flange 40, closer to the highest portion 50*b* of the peripheral edge. This arrangement can help prevent solution from pooling in the gap between the nozzle 38 and the peripheral edge highest portion 50*b* when dispensing the solution from the container 14.

In addition, the upper flange 40 preferably is not flat but is instead non-symmetrically tapered from the angled peripheral edge 50 to the generally vertical nipple 38. And the cover 42 has a peripheral edge 52 that defines a plane that is parallel to and has the same angle as the peripheral edge 50 of the upper flange 50, so that they mate with each other with the cover is closed. These features further improve the user's ability to view and direct the flow of dispensed lens care solution with the cover open and to protect the nipple from contaminants with the cover closed.

It will be understood that the cap 18 can be used on other containers for lens care solutions, including any of those described herein, as well as on containers for fluids other than lens care solutions. It will be further understood that the container 14 may be alternatively provided with a conventional cap for bottles for lens care solution. For example, the cap may be an interference-fit (snap-fit) cap, a pivotal snap-fit cap, or a screw cap. FIGS. 1, 2, 4, and 5 show details of the docking site for the lens case 12. The docking site is preferably configured to receive and releasably secure the lens case 12 in a generally horizontal position when the container 14 sits upright on a shelf, countertop, or other support surface. As used herein, "horizontal docking" refers to a lens case fitted to a docking site of a container in a way such that a platform of a docked lens case is substantially parallel to the bottom of the container. "Docking" refers to a process by which a lens case is securely but releasably fitted to an accessible site on a dispensing container, preferably by using manual force. It should be understood that the docked lens case may be released from the docking site, preferably by using manual force. The docking site may be integral with or releasably affixed to the container.

The docking site is preferably defined by or attached to the base 20 of the container 14. The base 20 is preferably removably coupled to the container hollow body 16 by a snap fitting 54. Alternatively, the base 20 can be fixedly attached to the container body by, for example, adhesives, solvent bonding, ultrasonic or thermal welding, connectors, or other attachment means; or the base portion can be integrally formed as part of a unitary container body.

In the depicted embodiment, the docking site comprises a chamber 56 defined by the base 20. The docking chamber 56 is in the form of a tunnel extending through the base 20 from one side to the other, with two side openings 58 in communication therewith for inserting and removing the lens case 12 from either side. The side openings 58 are preferably formed in a peripheral side wall 59 of the base, and extend around a portion of the base's sides, so that at least a portion of the lens case 12 is visible within the docking chamber 12 from any viewing angle around the container 14, and so that the user can more readily release the lens case from the chamber.

Alternatively, the docking site may be provided by an otherwise-configured chamber and opening at another location on the container. For example, the chamber may be in the form of a tunnel with two side openings, the first side opening sized and shaped for inserting and removing the lens case and the second side opening smaller. The smaller second side opening is not large enough for the lens case but instead is sized and shaped for inserting one or more fingers to push the lens case out through the first side opening.

The docking chamber 56 preferably has a dimension and shape to accommodate and mate with the lens case 12 so that the lens case can be conveniently and securely fitted into the docking chamber when not in use, but for use can be readily removed with light manual pressure by the user. In addition, the docking chamber 56 and the lens case 12 are preferably configured so that the lens case does not protrude out of the side openings 58, but instead the periphery of the lens case generally aligns with the general contour of the hollow body 16 and base 20 of the container 14 for aesthetic appeal.

FIGS. 1 and 10-13 show details of the lens case 12, which includes a main body 60 defining a pair of separate and discrete wells (e.g., cavities or reservoirs) 62, each configured to receive one contact lens and an amount of a lens care solution. Each well 62 has an open end that preferably has a substantially circular, oval, or rain-drop shaped periphery.

The lens case 12 further includes one or two caps 64 that are removably attached to the wells 62 at their open ends to provide a substantially liquid-impermeable seal. Preferably, the caps 64 each include a sealing rim or surface configured to sealingly mate with peripheral surfaces surrounding the wells 62. It should be understood that a lens case with a different design can alternatively be used.

The lens case 12 may be constructed of a material that is sturdy and impervious to chemicals contained in the lens care solution. For example, polystyrene, high-density polyethylene, or polypropylene can be the construction material of choice, although others may be used. It should be understood that a lens case with another design can alternatively be used. For example, the system could include one or two (or more) lens cases, each with only one well, for docking at one or two (or more) docking sites.

Referring now to FIGS. 1, 2, and 4-13, the system 10 additionally includes a retainer mechanism that releasably secures the lens case 12 in the docking chamber 15. In the depicted embodiment, the retainer mechanism includes a resiliently moveable engagement member 66 that interengages with a cooperating engagement surface 68 to retain the lens case 12 in the docking chamber 56. For example, the engagement member 66 may comprise a protrusion 67 such as a raised rib or finger extending into the docking chamber 56, and the engagement surface 68 may be a mating recess defined in the lens case 12, as shown. Preferably, the engagement member protrusion 67 positively engages and disengages the lens case engagement recess 68 with an audible or tactile "click" or other user-recognizable indicator of engagement and disengagement. And the main body 62 of the lens case 12 preferably has tapered ends 69, for example formed by the curvature of the wells 62, to facilitate resiliently deflecting the engagement member 66 out of the way when inserting the lens case into the docking chamber 56.

In addition, the engagement member protrusion 67 is preferably formed on, and at an end of, one or more resiliently flexing panels. For example, the engagement member protrusion 67 can be formed on and positioned between two resiliently flexing panels 72 extending from a lower chamber surface 70 of the base 20 or another portion of the container 14. Because the engagement member protrusion 67 extends upward from the lower chamber surface 70, the lens case engagement recess 68 is defined on the bottom of the main body 60 of the lens case 12 to provide the cooperative engagement.

Preferably, the engagement member panels 72 and protrusion 67 are integrally formed as a part of the unitary base 20. For example, the panels 72 and the protrusion 67 may be formed by a continuous sheet of material that has a generally uniform thickness and that remains between two slots 74 formed in the lower chamber surface 70 during the molding process. And the protrusion 67 is formed by a bulge made at about the longitudinal mid-point of the continuous sheet during the molding process, with the bulge dividing the sheet into two panels at a slight incline from the lower chamber surface 70.

Furthermore, the base 20 preferably has a peripheral base flange 76 extending downwardly from the lower chamber surface 70. The base flange 76 has a length selected to define a deflection space under the panels 72 sufficient to allow for the resilient deflection of the engagement member 66 out of the docking chamber 56 when the lens case 12 is inserted into it (see FIG. 8). In a typical commercial embodiment, for example, the base flange 76 is about 0.3-0.4 mm.

Figure 6:
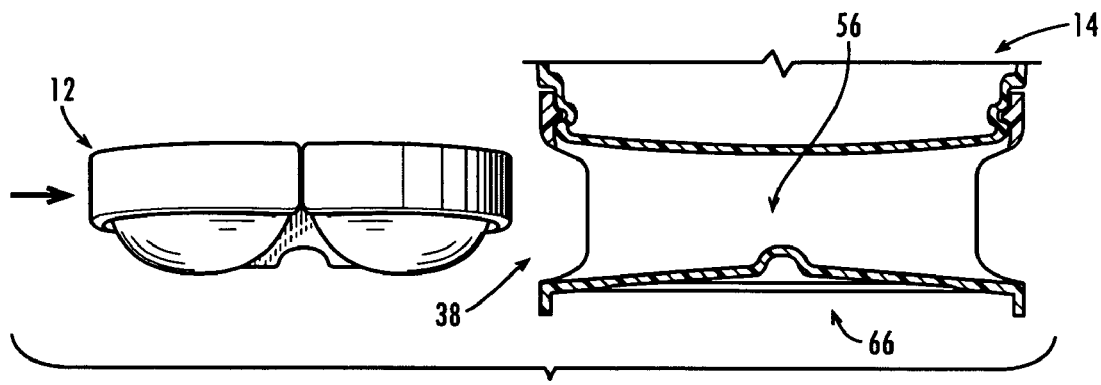
FIG. 6 is a schematic view of a lower portion of the lens care system of FIG. 1, showing the lens case ready for insertion into the docking chamber and the engagement member in the rest position.
Figure 7:
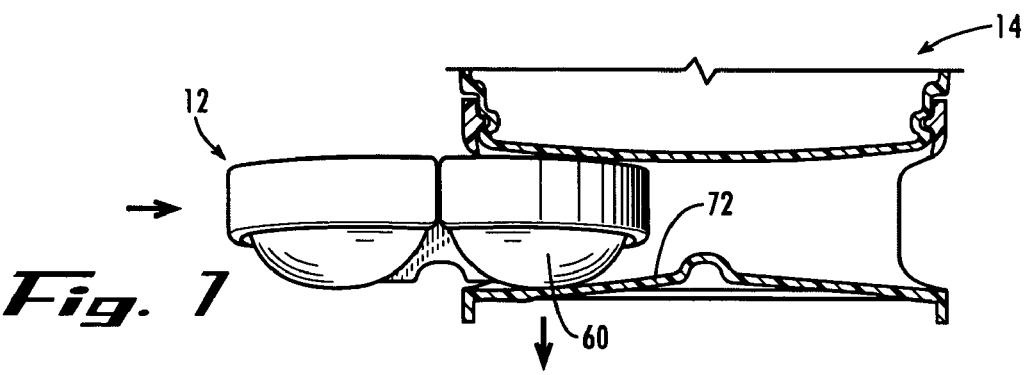
FIG. 7 is a schematic view of the lens care system portion of FIG. 6, showing the lens case partially inserted.
Figure 8:
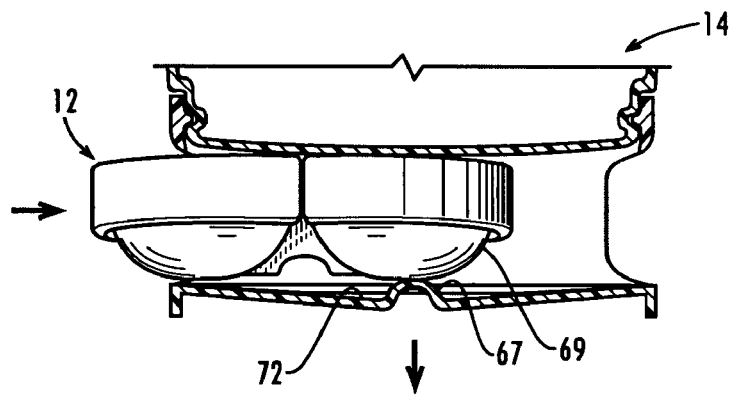
FIG. 8 is a schematic view of the lens care system portion of FIG. 6, showing the lens case inserted further and the engagement member in the deflected position.

FIGS. 6-9 show the lens case 12 being inserted into the docking chamber 56. In FIG. 6, the lens case 12 is aligned with the docking chamber 56 for lateral insertion through one of the side openings 58, with the engagement member 66 in the rest position (see also FIG. 1). In FIG. 7, the lens case 12 has been partially inserted, and the main body 60 of the lens case is contacting the first panel 72 and gradually forcing it downward out of the way. In FIG. 8, the lens case 12 has been inserted further, and the tapered end 69 of the lens case has engaged and forced the protrusion 67 downward out of the way. The engagement member 66 is now in the deflected position, with the protrusion 67 and the panels 72 moved out of the docking chamber 56 and into the deflection space formed by the downwardly extending base flange 76.

Figure 9:
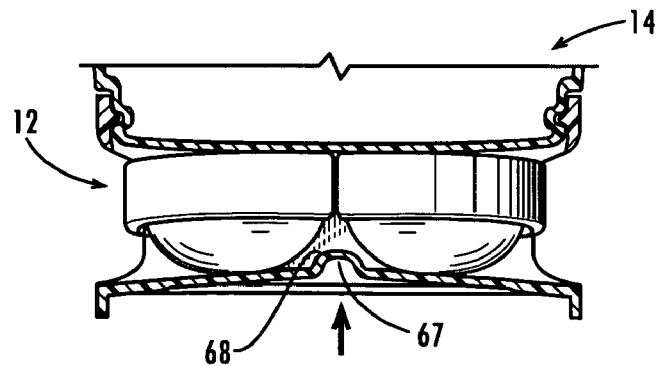
FIG. 9 is a schematic view of the lens care system portion of FIG. 6, showing the lens case fully inserted and secured in a docking position.
Figure 10:
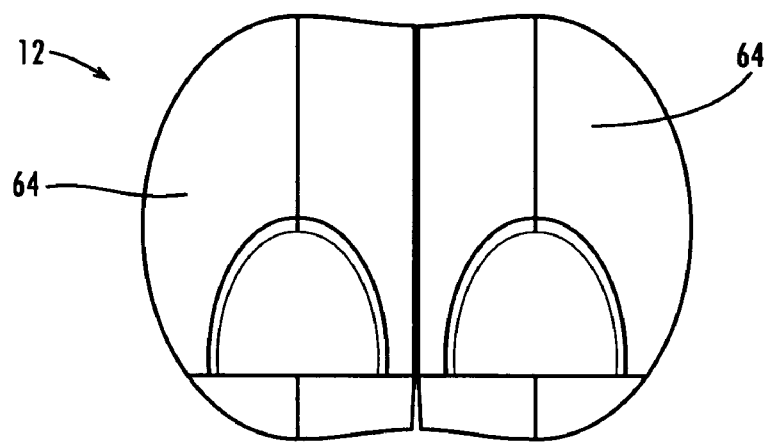
FIG. 10 is a plan view of the lens case of FIG. 1.
Figure 11:
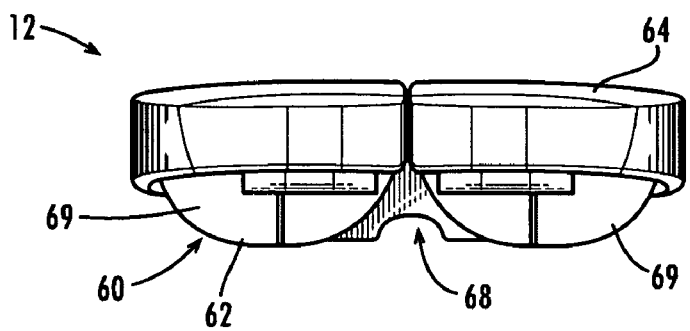
FIG. 11 is a front elevation view of the lens case of FIG. 10, showing the engagement recess in the main body.
Figure 12:
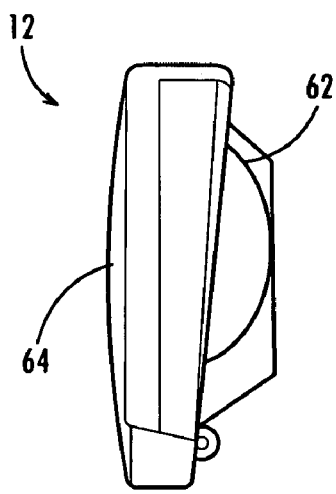
FIG. 12 is a right side elevation view of the lens case of FIG. 10.
Figure 13:
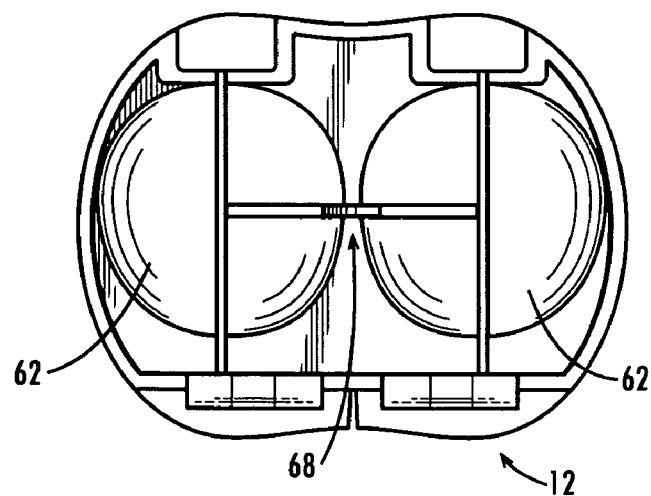
FIG. 13 is a bottom view of the lens case of FIG. 10.

FIG. 9 shows the lens case 12 fully inserted into the docking chamber 56 in a docking position (see also FIG. 9). The panels 72 have resiliently returned to an engagement position with the engagement member protrusion 67 interengaged in the lens case engagement recess 68 to secured the lens case 12 in the docking chamber 56. When the lens case 12 is removed from the docking chamber 56, the lens case engagement recess 68 is forced from interengagement with the engagement member protrusion 67, and the engagement member 66 resiliently returns to the rest position of FIG. 6.

The material and thickness selected for the engagement member 66 permit the panels 72 to hingedly move relative to the lower chamber surface 70 (at one end) and to hingedly move relative to the protrusion 67 (at the other end), without breaking from normal use. In addition, the panels 72 and protrusion 67 are resiliently flexible. Because of the flexibility of the engagement member 66, the panels curve slightly (along their length) and/or the protrusion bends slightly (to decrease its radius) as the engagement member 66 moves between the rest position of FIG. 6 and the deflected position of FIG. 8. And because of the resiliency of the engagement member 66, when it is in the flexed engagement position of FIG. 9, it stores a charge sufficient to bias the engagement protrusion 67 into the engagement recess 68 to assist in securing the lens case 12 in the docking chamber 56.

The present invention includes a number of alternative retainer mechanism designs. In one alternative embodiment, the resiliently moveable engagement member extends downward into the docking chamber from the bottom wall of the hollow body or from a top chamber surface, and the cooperating engagement recess is defined in the top of the lens case. In another alternative embodiment, the resiliently moveable engagement member extends laterally into the docking chamber from the side wall of the base, with the cooperating engagement recess defined in the side of the lens case. In addition, the engagement member protrusion can be positioned projecting into the docking chamber at about its longitudinal mid-point (e.g., between two resiliently flexing panels), with the cooperating engagement recess positioned between the wells of the lens case. Or the engagement member protrusion can be positioned projecting into the docking chamber at one end adjacent one of the side wall openings (e.g., at one end of a single resiliently flexing panel), with the cooperating engagement recess positioned at one side or end of the lens case. And in yet other alternative embodiments, the retainer mechanism includes two or more engagement members extending into the docking chamber from its top, bottom, one side, both sides, or a combination thereof.

In other alternative embodiments the moveable engagement member includes the protrusion between two panels, and the panels are hingedly movable but not necessarily resiliently flexing. For example, the outer end of one of the panels may be unattached to the lower chamber surface, and instead it rides along a guide track in or on the chamber surface. As another example, the two panels extend inwardly toward each other where they have protruding portions at their free ends, which cooperate to from the engagement protrusion. And as still another example, a spring element is positioned under the panels to bias the engagement protrusion into engagement with the lens case engagement recess.

In still other alternative embodiments, the resiliently moveable engagement member is a push button. The spring-biased push button comprises a protrusion/button that has a circular, elongated, or other regular or irregular shape, that extends into the chamber through an opening with a similar shape, that interengages an engagement recess with a similar shape in the lens case, and that is biased into the chamber by a helical, leaf or other spring element.

And in another alternative embodiment, the resiliently moveable engagement member extends from the lens case and the cooperating engagement surface is defined in the docking chamber. And in yet another alternative embodiment, the engagement member protrusion of the docking chamber and the engagement recess of the lens case are arranged in other configurations to form mating male and female snap fittings to safely secure the docked lens case.

Further alternative embodiments may include a hinged retainer door that covers the docking chamber and has a snap-lock closure, and a retainer drawer that holds the lens case and slides into and out of the docking chamber.

FIGS. 16-19 show a lens care system 110 according to a second example embodiment. This system 110 is similar to the system 10 of the first embodiment, in that it includes a lens case 112, a container 114 having a hollow body 116, a cap 118, a base 120, and a docking chamber 156 for the lens case, and a retainer mechanism having an engagement member 166 in a docking chamber.

In this embodiment, however, the container hollow body 116 has a recessed gripping surface 128 defining a circumferential notch. In addition, the cap 118 and hollow body 116 are configured to cooperatively form a smooth, continuously sloped outer surface. And the lens case 112 is of a different but conventional type having a main body with a flat platform and having screw-on caps for the wells, with the engagement recess 168 formed in the platform from one side to the other.

FIGS. 20-26 show a lens care system 210 according to a third example embodiment. This system 210 is similar to the lens care systems of the first and second embodiments, in that it includes a lens case 212 and a container 214 having a hollow body 216, a cap 218, a base 220, and a docking chamber 256 for the lens case.

In this embodiment, however, the docking chamber 256 is in the form of a cave defined in the container body 216, has only one open side 258 which is formed in the broader front face 222a and in a portion of the side walls 222c and 222d of the container body, and is longer for receiving the lens case 212 transversely (both wells 262 inserted into the chamber simultaneously, as shown). In addition, the container base 220 is integrally formed with the hollow body 216 as a single piece, the cap 218 is a screw-on cap, and the lens case 212 is held in the docking chamber 256 by a frictional interference fit.

Furthermore, the lens case 212 includes an additional feature well suited for use with the integrated lens care system 210, as shown in FIGS. 23-26. The main body 260 of the lens case 212 includes a platform having an edge portion 261 configured to serve as a "handle" that can be grasped (e.g., by the thumb and forefinger) to direct manual force to push in or pull out the lens case 212 from the docking chamber 256. For example, the edge handle 261 may be positioned between the wells 262 and extend outwardly from the body 260, so the edge handle is easily accessible when the lens case 212 is in the docking chamber 256. And the edge portion 261 may extend upwardly from the body/platform with a generally semi-circular profile in both a plan view (see FIG. 23) and an elevation view (see FIG. 24), thereby having the general shape of one quarter of a sphere. This configuration provides a smoothly curved location that nicely receives one of the user's fingers for grasping the lens case 212. In addition, this upwardly extending edge 261 can double as a lens case engagement recess when including a retainer mechanism with an engagement member positioned adjacent the chamber side opening.

The platform of the body 260 is preferably substantially flat, which is beneficial for maintaining the lens case 212 in stable position on a flat surface (e.g., on a countertop or table). However, the body/platform can alternatively have curved surfaces.

FIGS. 27 and 28 show a lens care system 310 according to a fourth example embodiment. This system 310 is similar to the lens care systems of the other described embodiments, in that it includes a lens case 312 and a container 314 having a hollow body 316, a cap (not shown), a base 320, and a docking chamber 356 for the lens case. In this embodiment, however, the retainer mechanism includes engagement protrusions 367 extending laterally inward from the base side wall 359 that interengage with cooperating engagement recesses 368 formed in the lens case caps 264.

FIGS. 29-33 show a lens care system 410 according to a fifth example embodiment. This system 410 is similar to the lens care systems of the other described embodiments, in that it includes a lens case 412 and a container 414 having a hollow body 416 and a docking site for the lens case.

In this embodiment, however, the lens case 412 removably attaches to the container body 416 to cover the dispensing opening, thereby also serving as the closure cap for the container 414. The lens case 412 includes the main body 460, the wells 462, and one cap 464 for both wells, though two caps can be provided, if desired. Preferably, the cap 464 is pivotally coupled to the main body by a hinge coupling 480 and has an openable snap closure 482.

Preferably, the retainer mechanism for removably attaching the lens case 412 to the container body 416 comprises a snap fitting. For example, the container body 414 may have an engagement member provided by an upper continuous depression 480 around its peripheral edge that positively engages an engagement surface formed by a lower peripheral edge of the side wall of the main body 460 of the lens case 412 with a snap fit. So the docking site in this embodiment is the upper periphery 480 of the container 414. Alternatively, or additionally, the retainer mechanism may include one or more conventional twist-and-lock fittings for removably attaching the lens case 412 to the container body 416. The container body 416 and the lens case 412 are preferably configured so that the periphery of the lens case generally aligns with the general contour of the hollow body of the container for aesthetic appeal.

In addition, the container 414 includes an upright neck 426 defining an opening for dispensing the lens care solution from the container body 416. The main body 460 of the lens case 412 includes a recessed portion 484 that receives the upright neck 426 and covers it when the lens case is mounted in the docked position and when the lens case is removed for use. The recessed portion 484 of the lens case 412 preferably has a shape to conform to the shape of the neck, for example, it may be dome-shaped, as shown. And the recessed portion 484 is preferably positioned between the wells 462, to minimize the height of the lens case 412.

Accordingly, the present invention provides a number of advantages over known systems. The retainer mechanism permits holding the components securely together in a configuration having an aesthetic, uniform shape, and then removing them for use, which provides enhanced user convenience when handling and storing the components. In addition, the components of the invention are useful independent of one another. Thus, once a lens care solution container is empty, the solution container may be discarded and a replaced with a new solution container.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Furthermore, titles, headings, or the like are provided to enhance the reader's comprehension of this document, and should not be read as limiting the scope of the present invention. Accordingly, the spirit and scope of the appended claims should not be limited to the description of the preferred versions contained therein.

What is claimed is:

1. A lens care system for use with at least one ophthalmic lens and a lens care solution, the system comprising:
a lens case for the lens;
a container for the solution, the container including a docking site for storing the lens case; and
a retainer mechanism including an engagement surface and a movable engagement member that positively engages the engagement surface to retain the lens case to the container at the docking site, wherein the engagement member comprises at least one panel and a protrusion, wherein the protrusion is formed at an end of the panel, wherein the engagement surface comprises an engagement recess that positively engages the engagement member protrusion, wherein the docking site comprises a chamber for receiving the lens case and the at least one panel extends from a lower chamber surface into the chamber.

2. The system of claim 1, wherein the container comprises a hollow body for containing the solution and a base including the docking site.

3. The system of claim 2, wherein the base is removably coupled to the hollow body.

4. The system of claim 1, wherein the docking site comprises a chamber defined by the container and configured for receiving the lens case therein.

5. The system of claim 4, wherein the docking chamber is in the form of a tunnel or a cave.

6. The system of claim 1, wherein the engagement member extends from the container at the docking site and the engagement surface is defined by the lens case.

7. The system of claim 6, wherein the lens case comprises two of the wells and the engagement recess is between the wells.

8. The system of claim 6, wherein the lens case has at least one tapered end to deflect the engagement member out of the way when docking the lens case.

9. The system of claim 1, wherein the at least one panel is resiliently flexible and moves between a rest position with the protrusion extending into the chamber and a deflected position with the engagement member flexed and the protrusion deflected at least partially out of the chamber.

10. The system of claim 9, wherein the container further comprises a downwardly extending base flange defining a deflection space below the at least one panel, wherein the deflection space receives at least a portion of the protrusion when the engagement member is in the deflected position.

11. The system of claim 1, wherein the engagement member comprises two panels with the protrusion between the panels.

12. The system of claim 1, wherein the panel is defined between two slots formed in the lower chamber surface.

13. A lens care system for use with at least one ophthalmic lens and a lens care solution, the system comprising:
  a lens case for the lens, the lens case defining an engagement surface recess; and
  a container for the solution, the container defining a docking chamber for receiving the lens case, the container having a resiliently flexible engagement member including at least one panel and a protrusion formed on the panel, wherein the chamber is partially defined by a lower chamber surface, and the at least one panel extends upwardly from the lower chamber surface, wherein the engagement member resiliently moves between a rest position with the protrusion extending into the chamber, a deflected position with the engagement member flexed and the protrusion deflected at least partially out of the chamber, and an engaged position with the protrusion positively engaging the engagement surface recess to retain the lens case in the chamber.

14. The system of claim 13, wherein the engagement member comprises two panels with the protrusion between the panels.

15. The system of claim 13, wherein the at least one panel is defined between two slots formed in the lower chamber surface.

16. The system of claim 13, wherein the at least one panel and the protrusion are integrally formed with the lower chamber surface, wherein the at least one panel and the protrusion are formed by a continuous sheet of material that remains between two slots formed in the lower chamber surface.

17. The system of claim 16, wherein the protrusion is formed by a bulge at about the longitudinal mid-point of the continuous sheet, with the bulge dividing the sheet into two panels at an incline from the lower chamber surface.

18. The system of claim 13, wherein the container further comprises a downwardly extending base flange defining a deflection space below the at least one panel, wherein the deflection space receives at least a portion of the protrusion when the engagement member is in the deflected position.

19. The system of claim 13, wherein the docking chamber and the lens case are configured so that the lens case does not protrude out of the chamber, but instead a periphery of the lens case generally aligns with a general contour of the container to provide the appearance of a continuous surface for aesthetic appeal.

20. A container for a lens care solution and for use in a lens care system including a lens case, the container comprising:
  a docking chamber for receiving the lens case in an openly accessible position; and a resiliently flexible engagement member including at least one panel and a protrusion formed at an end of the panel, wherein the chamber is partially defined by a lower chamber surface, and the at least one panel extends upwardly from the lower chamber surface, wherein the engagement member resiliently moves between a rest position with the protrusion extending into the chamber, a deflected position with the engagement member flexed and the protrusion deflected at least partially out of the chamber, and an engaged position with the protrusion positively engaging an engagement surface recess of the lens case to retain the lens case in the chamber.

21. The container of claim 20, wherein the engagement member further comprises two panels with the protrusion between the panels.

22. The container of claim 20, wherein the at least one panel is defined between two slots formed in the lower chamber surface.

23. The container of claim 20, wherein the at least one panel and the protrusion are integrally formed with the lower chamber surface, wherein the at least one panel and the protrusion are formed by a continuous sheet of material that remains between two slots formed in the lower chamber surface.

24. The container of claim 23, wherein the protrusion is formed by a bulge at about the longitudinal mid-point of the continuous sheet, with the bulge dividing the sheet into two panels at an incline from the lower chamber surface.

25. The container of claim 20, wherein the container further comprises a downwardly extending base flange defining a deflection space below the at least one panel, wherein the deflection space receives at least a portion of the protrusion when the engagement member is in the deflected position.

26. The container of claim 20, wherein the container includes two opposing side walls each defining an inwardly recessed portion for gripping.

27. The container of claim 26, wherein the recessed gripping portions have surface irregularities for increased gripping friction.

28. A lens care system for use with at least one ophthalmic lens and a lens care solution, the system comprising:
  a lens case for the lens;
  a container for the solution, the container including a docking site for storing the lens case; and
  a retainer mechanism including an engagement surface and a movable engagement member that positively engages the engagement surface to retain the lens case to the container at the docking site wherein the engagement member comprises two panels and a protrusion, wherein the protrusion is formed at an end of the panel and between the two panels, and the engagement surface comprises an engagement recess that positively engages the engagement member protrusion.

29. The system of claim 28, wherein the container comprises a hollow body for containing the solution and a base including the docking site.

30. The system of claim 29, wherein the base is removably coupled to the hollow body.

31. The system of claim 28, wherein the docking site comprises a chamber defined by the container and configured for receiving the lens case therein.

32. The system of claim 28, wherein the engagement member extends from the container at the docking site and the engagement surface is defined by the lens case.

33. The system of claim 32, wherein the lens case comprises two of the wells and the engagement recess is between the wells.

34. The system of claim 32, wherein the lens case has at least one tapered end to deflect the engagement member out of the way when docking the lens case.

35. The system of claim 28, wherein the at least one panel is resiliently flexible and moves between a rest position with the protrusion extending into the chamber and a deflected position with the engagement member flexed and the protrusion deflected at least partially out of the chamber.

36. The system of claim 28, wherein the container further comprises a downwardly extending base flange defining a deflection space below the at least one panel, wherein the deflection space receives at least a portion of the protrusion when the engagement member is in the deflected position.

37. A lens care system for use with at least one ophthalmic lens and a lens care solution, the system comprising:
   a lens case for the lens, the lens case defining an engagement surface recess; and
   a container for the solution, the container defining a docking chamber for receiving the lens case, the container having a resiliently flexible engagement member including two panels and a protrusion formed between the panels, wherein the engagement member resiliently moves between a rest position with the protrusion extending into the chamber, a deflected position with the engagement member flexed and the protrusion deflected at least partially out of the chamber, and an engaged position with the protrusion positively engaging the engagement surface recess to retain the lens case in the chamber.

38. The system of claim 37, wherein the container further comprises a downwardly extending base flange defining a deflection space below the at least one panel, wherein the deflection space receives at least a portion of the protrusion when the engagement member is in the deflected position.

39. The system of claim 37, wherein the docking chamber and the lens case are configured so that the lens case does not protrude out of the chamber, but instead a periphery of the lens case generally aligns with a general contour of the container to provide the appearance of a continuous surface for aesthetic appeal.

40. A container for a lens care solution and for use in a lens care system including a lens case, the container comprising:
   a docking chamber for receiving the lens case in an openly accessible position; and a resiliently flexible engagement member including two panels and a protrusion formed between the panels, wherein the engagement member resiliently moves between a rest position with the protrusion extending into the chamber, a deflected position with the engagement member flexed and the protrusion deflected at least partially out of the chamber, and an engaged position with the protrusion positively engaging an engagement surface recess of the lens case to retain the lens case in the chamber.

41. The container of claim 40, wherein the chamber is partially defined by a lower chamber surface, and the at least one panel extends upwardly from the lower chamber surface.

42. The container of claim 40, wherein the container further comprises a downwardly extending base flange defining a deflection space below the at least one panel, wherein the deflection space receives at least a portion of the protrusion when the engagement member is in the deflected position.

43. The container of claim 40, wherein the container includes two opposing side walls each defining an inwardly recessed portion for gripping.

44. The container of claim 43, wherein the recessed gripping portions have surface irregularities for increased gripping friction.

45. A container for a lens care solution and for use in a lens care system including a lens case, the container comprising:
   a docking chamber for receiving the lens case in an openly accessible position; and a resiliently flexible engagement member including at least one panel and a protrusion formed at an end of the panel, wherein the engagement member resiliently moves between a rest position with the protrusion extending into the chamber, a deflected position with the engagement member flexed and the protrusion deflected at least partially out of the chamber, and an engaged position with the protrusion positively engaging an engagement surface recess of the lens case to retain the lens case in the chamber, wherein the container further comprises a downwardly extending base flange defining a deflection space below the at least one panel, wherein the deflection space receives at least a portion of the protrusion when the engagement member is in the deflected position.

46. The container of claim 45, wherein the engagement member further comprises two panels with the protrusion between the panels.

47. The container of claim 45, wherein the chamber is partially defined by a lower chamber surface, and the at least one panel extends upwardly from the lower chamber surface.

48. The container of claim 47, wherein the at least one panel is defined between two slots formed in the lower chamber surface.

49. The container of claim 47, wherein the at least one panel and the protrusion are integrally formed with the lower chamber surface, wherein the at least one panel and the protrusion are formed by a continuous sheet of material that remains between two slots formed in the lower chamber surface.

50. The container of claim 49, wherein the protrusion is formed by a bulge at about the longitudinal mid-point of the continuous sheet, with the bulge dividing the sheet into two panels at an incline from the lower chamber surface.

* * * * *